(12) United States Patent
Melamed et al.

(10) Patent No.: US 11,170,503 B2
(45) Date of Patent: Nov. 9, 2021

(54) SYSTEMS AND METHODS FOR DETECTION LIKELIHOOD OF MALIGNANCY IN A MEDICAL IMAGE

(71) Applicant: International Business Machines Corporation, Armonk, NY (US)

(72) Inventors: Roie Melamed, Haifa (IL); Lior Ness, Ra'anana (IL)

(73) Assignee: International Business Machines Corporation, Armonk, NY (US)

( * ) Notice: Subject to any disclaimer, the term of this patent is extended or adjusted under 35 U.S.C. 154(b) by 72 days.

(21) Appl. No.: 16/668,052

(22) Filed: Oct. 30, 2019

(65) Prior Publication Data

US 2021/0133954 A1  May 6, 2021

(51) Int. Cl.
*G06T 7/00* (2017.01)
*A61B 6/00* (2006.01)
(Continued)

(52) U.S. Cl.
CPC .......... *G06T 7/0012* (2013.01); *A61B 5/7267* (2013.01); *A61B 6/502* (2013.01);
(Continued)

(58) Field of Classification Search
None
See application file for complete search history.

(56) References Cited

U.S. PATENT DOCUMENTS 6,463,438 B1 * 10/2002 Veltri .................. G06K 9/0014
706/15
10,055,551 B2   8/2018 Agaian et al.
(Continued)

FOREIGN PATENT DOCUMENTS

WO       2018189549       10/2018
WO    WO-2019104221 A1 *  5/2019 ........... A61B 5/0091

OTHER PUBLICATIONS

Ran Bakalo et al., "A dual branch deep neural network for classification and detection in mammograms", arXiv, May 8, 2019 (Year: 2019).*
(Continued)

*Primary Examiner* — Vu Le
*Assistant Examiner* — Courtney Joan Nelson
(74) *Attorney, Agent, or Firm* — Roy S. Melzer

(57) ABSTRACT

There is provided a computer implemented method for detection of likelihood of malignancy in an anatomical image of a patient for treatment planning, comprising: receiving an anatomical image, feeding the anatomical image into a global component of a model trained to output a global classification label, feeding the anatomical image into a local component of the model trained to output a localized boundary, feeding the anatomical image patch-wise into a patch component of the model trained to output a patch level classification label, extracting a respective set of regions of interest (ROIs) from each one of the components, each ROI indicative of a region of the anatomical image likely to include an indication of malignancy, aggregating the ROIs from each one of the components into an aggregated set of ROIs, and feeding the aggregated set of ROIs into an output component that outputs an indication of likelihood of malignancy.

20 Claims, 6 Drawing Sheets

(51) Int. Cl.
    *A61B 5/00*           (2006.01)
    *G06K 9/32*           (2006.01)
    *G06K 9/34*           (2006.01)
    *G06N 20/00*         (2019.01)
    *G06K 9/46*           (2006.01)

(52) U.S. Cl.
    CPC .......... *A61B 6/5217* (2013.01); *G06K 9/3233* (2013.01); *G06K 9/34* (2013.01); *G06K 9/4652* (2013.01); *G06N 20/00* (2019.01); *G06T 2207/20081* (2013.01); *G06T 2207/30061* (2013.01); *G06T 2207/30068* (2013.01); *G06T 2207/30096* (2013.01)

(56) References Cited

U.S. PATENT DOCUMENTS

| | | | | |
|---|---|---|---|---|
| 2015/0213302 | A1* | 7/2015 | Madabhushi | G06K 9/00147 |
| | | | | 382/133 |
| 2017/0287134 | A1* | 10/2017 | Abedini | G06T 7/187 |
| 2018/0214105 | A1* | 8/2018 | Anavi | G06N 20/10 |
| 2019/0030371 | A1* | 1/2019 | Han | G16H 50/20 |
| 2019/0110753 | A1* | 4/2019 | Zhang | G16H 50/20 |

OTHER PUBLICATIONS

Ran Bakalo et al., "A dual branch deep neural network for classification and detection in mammograms", arXiv, May 8, 2019.

\* cited by examiner

SYSTEMS AND METHODS FOR DETECTION LIKELIHOOD OF MALIGNANCY IN A MEDICAL IMAGE

BACKGROUND

The present invention, in some embodiments thereof, relates to analysis of medical images and, more specifically, but not exclusively, to systems and methods for detection of likelihood of malignancy in a medical image.

Medical images, such as x-rays, mammograms, CT scans, and MRIs, are used routinely, generating a large volume of images. Radiologists manually sort through each one of the images in an effort to find visual findings, for example, indicative of cancer.

In one example, mammograms are used in a routine screening program in an attempt to detect breast cancer at an early stage. Radiologists manually review the mammographic images in an attempt to identify visual findings that are correlated with breast cancer. In another example, low dose CT scans of the chest are used in a routine screening program in an attempt to detect lung cancer at an early stage. Radiologists manually review each slice in an attempt to identify visual findings that are correlated with lung cancer.

Processes for automated analysis of anatomical images to identify visual findings are sought, for example, to assist the radiologist by flagging relevant anatomical images for closer inspection.

SUMMARY

According to a first aspect, a computer implemented method for detection of likelihood of malignancy in an anatomical image of a patient for planning treatment thereof, comprises: receiving an anatomical image, feeding the anatomical image into a global component of a model trained to output a global classification label, feeding the anatomical image into a local component of the model trained to output a localized boundary, feeding the anatomical image patch-wise into a patch component of the model trained to output a patch level classification label, extracting a respective set of regions of interest (ROIs) from each one of the components, each ROI indicative of a region of the anatomical image likely to include an indication of malignancy, aggregating the ROIs from each one of the components into an aggregated set of ROIs, and feeding the aggregated set of ROIs into an output component that outputs an indication of likelihood of malignancy, wherein treatment of the patient is planned according to the indication.

According to a second aspect, a computer implemented method for training a model for detection of an indication of malignancy in an anatomical image of a target individual, comprises: training a global component of the model using a set of training images each labeled with an image level classification label, training a local component of the model using a set of training images each annotated with a localized boundary denoting a location associated with likelihood of malignancy, training a patch component of the model using a set of training images each divided into a plurality of patches associated with corresponding patch level classification labels, training an output component of the model using a set of training aggregated regions of interest (ROIs) created by aggregating ROIs extracted from each one of the components, each ROI indicative of a region of the anatomical image having likelihood of malignancy, and associated ground truth labels, and providing the global, local, patch, and output components of the model, wherein in response to feeding a target anatomical image into the model, the output component outputs an indication of the likelihood of malignancy.

According to a third aspect, a system for detection of likelihood of malignancy in an anatomical image of a patient for planning treatment thereof, comprises: at least one hardware processor executing a code for: receiving an anatomical image, feeding the anatomical image into a global component of a model trained to output a global classification label, feeding the anatomical image into a local component of the model trained to output a localized boundary, feeding the anatomical image patch-wise into a patch component of the model trained to output a patch level classification label, extracting a respective set of regions of interest (ROIs) from each one of the components, each ROI indicative of a region of the anatomical image likely to include an indication of malignancy, aggregating the ROIs from each one of the components into an aggregated set of ROIs, and feeding the aggregated set of ROIs into an output component that outputs an indication of likelihood of malignancy, wherein treatment of the patient is planned according to the indication.

In a further implementation of the first, second, and third aspects, the anatomical image comprises a mammographic image, and likelihood of malignancy comprises likelihood of breast cancer.

In a further implementation of the first, second, and third aspects, a same number of ROIs extracted for each one of the global component, the local component, and the patch component.

In a further implementation of the first, second, and third aspects, a number of ROIs in the aggregated set is between the same number and three times the same number.

In a further implementation of the first, second, and third aspects, the aggregation of the ROIs is performed by at least one of an intersection operation and a union operation, performed on the ROIs from each one of the components.

In a further implementation of the first, second, and third aspects, the output component outputs a score indicative of likelihood of malignancy for the anatomical image as a whole.

In a further implementation of the first, second, and third aspects, ROIs extracted for each one of the components are disjoint, without an intersection between ROIs extracted for each one of the components.

In a further implementation of the first, second, and third aspects, each ROIs is associated with a score indicative of likelihood of malignancy depicted therein, wherein each aggregated ROI includes a vector of scores of the respective components, and wherein the vector is fed into the output component, wherein the output component computes an aggregation score for each aggregation ROI indicative of likelihood of malignancy for the respective aggregation ROI.

In a further implementation of the first, second, and third aspects, the global component includes a global pooling operation layer after which the ROIs cannot be detected.

In a further implementation of the first, second, and third aspects, the ROIs of the global component are computed by a fully-convolutional classifier after the global pooling operation layer, and re-applying the fully-convolutional classifier at each location of the last feature map.

In a further implementation of the first, second, and third aspects, the ROIs of the global component are computed by a back propagation method.

In a further implementation of the first, second, and third aspects, the ROIs of the global component are computed by occluding different areas of the anatomical image and re-running the anatomical image with occluded area through the global component to determine which occluded areas correlate with the largest difference in score indicative of malignancy.

In a further implementation of the first, second, and third aspects, a number of neural network layers of the patch component is higher than a number of neural network layers of the global component and is higher than a number of neural network layers of the local component.

In a further implementation of the first, second, and third aspects, each one of the global component, the local component, the patch component, and the output component are implemented as neural networks.

In a further implementation of the first, second, and third aspects, each one of the global component, local component, and patch component are trained independently.

In a further implementation of the third aspect, the at least one hardware processor further executes a code for: training the global component of the model using a set of training images each labeled with an image level classification label, training the local component of the model using a set of training images each annotated with a localized boundary denoting a location associated with likelihood of malignancy, training the patch component of the model using a set of training images each dividing into a plurality of patches associated with corresponding patch level classification labels, and training the output component of the model using a set of training aggregated regions of interest (ROIs) created by aggregating ROIs extracted from each one of the components and an image level classification label.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In the drawings.

DETAILED DESCRIPTION

Figure 1:
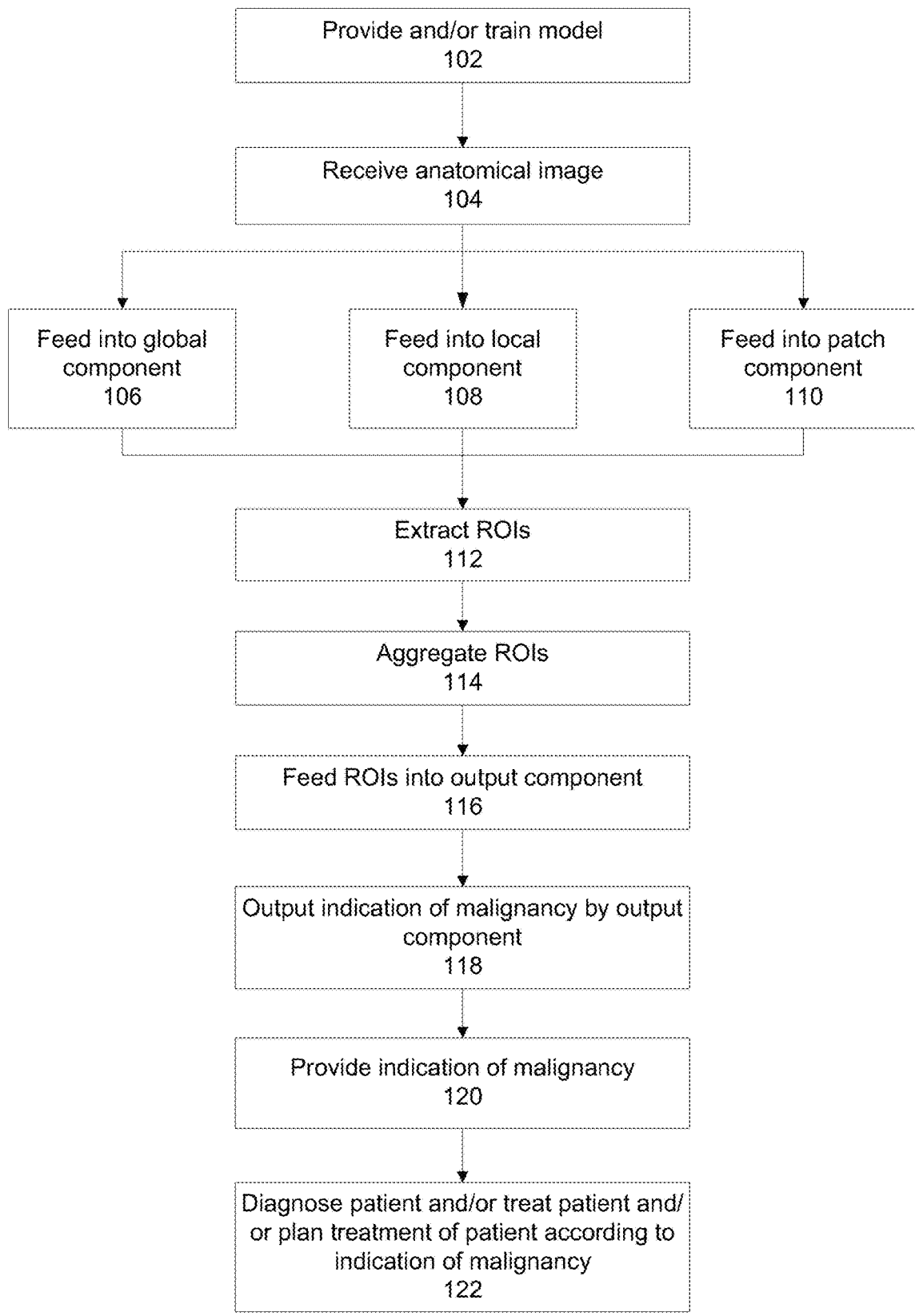
FIG. 1 is a flowchart of a method for detection of likelihood of malignancy in an anatomical image of a patient by a model including a global component, a local component, a patch component, and an output component that is fed aggregated ROIs extracted from each of the other components, in accordance with some embodiments of the present invention.

The present invention, in some embodiments thereof, relates to analysis of medical images and, more specifically, but not exclusively, to systems and methods for detection of likelihood of malignancy in a medical image.

An aspect of some embodiments of the present invention relates to systems, methods, an apparatus, and/or code instructions (e.g., stored in a memory and/or data storage device and executable by one or more hardware processors) for detecting likelihood of malignancy in an anatomical image by a model that includes a global component trained to output a global classification indicative of likelihood of malignancy for the anatomical image as a whole, a local component trained to output a localized boundary denoting location indicating likelihood of malignancy within the anatomical image, and a patch component trained to output a patch level classification level for each patch of the anatomical image. The anatomical image is fed as a whole into the global component and into the local component, and fed patch-wise into the patch component. Each of the global, local, and patch components of the model independently process the image (or patch of the image). A respective set of regions of interest (ROIs) is extracted from each one of the global, local, and patch components of the model. Each ROI is indicative of a region of the anatomical image likely to include an indication of malignancy. The ROIs from each one of the components are aggregated into an aggregated set of ROIs, optionally by performing a union and/or intersection operation on the ROIs. The aggregated set of ROIs are fed into an output component that outputs an indication of likelihood of malignancy. The patient may be diagnosed according to the indication, and/or treatment of the patient may be planned according to the indication, for example, additional imaging of the patient may be performed, a biopsy may be performed, surgery may be performed, chemotherapy may be administered, radiation therapy may be administered, and/or a watch and wait approach may be selected.

An aspect of some embodiments of the present invention relates to systems, methods, an apparatus, and/or code instructions (e.g., stored in a memory and/or data storage device and executable by one or more hardware processors) for training a model for detecting likelihood of malignancy in an anatomical image, where the model includes a global component trained to output a global classification indicative of likelihood of malignancy for the anatomical image as a whole, a local component trained to output a localized boundary denoting location indicating likelihood of malignancy within the anatomical image, and a patch component trained to output a patch level classification level for each patch of the anatomical image. Each of the global, local, and patch components of the model may be independently trained, for example, each component is trained using its own dedicated loss function and/or data computed within each component does not flow to other components. The global component of the model is trained using a set of training images each labeled with an image level (i.e., global) classification label. The local component of the model is trained using a set of training images each annotated with a localized boundary denoting a location associated with likelihood of malignancy. The patch component of the model is trained using a set of training images each divided into multiple patches associated with corresponding patch level classification labels. An output component of the model is trained using a set of training aggregated ROIs created by aggregating ROIs extracted from each one of global, local, and patch components, and associated ground truth labels. Each ROI is indicative of a region of the anatomical image having likelihood of malignancy. The global, local, patch, and output components of the model are provided. In response to feeding a target anatomical image into the model, the output component outputs an indication of the likelihood of malignancy.

It is noted that as described herein, detecting likelihood of malignancy for a certain image may sometimes refer to detection of one or more visual findings in the image that are correlated with likelihood of malignancy. Such visual findings may be analyzed by a radiologist.

At least some implementations of the systems, methods, apparatus, and/or code instructions described herein improve the technology of machine learning processes for automated detection of likelihood of malignancy depicted by a medical image, for example, likelihood of breast cancer depicted in a mammogram, and likelihood of lung cancer depicted by a low dose CT scan. Existing models (e.g., deep learning solutions for computed aided diagnosis (CAD)) are based on a single classifier, on either local object detector type model (i.e., that is trained on locally annotated data) or a global image classification type model (i.e., that is trained on global or per-image annotations). The ensemble of multiple different types of neural networks components described herein improves on the existing models, for example, providing a relatively higher rate of detection and/or relatively higher probability of accuracy.

At least some implementations of the systems, methods, apparatus, and/or code instructions described herein improve the technology of machine learning processes by addressing the technical problem of creating a single output from an ensemble of multiple different types of neural networks, in particular, obtaining a single indication of likelihood of malignancy. The technical problem arises in obtaining a single output result from different neural networks that generate different outputs. For example, a local network may follow the general framework of a bounding-box object detector (e.g, RetinaNet, YOLO, SSD) and outputs a malignancy score per different image locations, whereas a global network (i.e., which learns from weakly labeled whole images) outputs an overall classification label for the image as a whole. The technical improvement (i.e., solution) provided by at least some implementations of the systems, methods, apparatus, and/or code instructions described herein is based on extracting ROIs of the image denoting likelihood of malignancy from each one of the different neural network components of a machine learning model. The identified ROIs are combined and fed into another neural network component of the model that provides the final output indicative of where in the image likelihood of malignancy is detected, for example, where in the mammogram image is there a likelihood of breast cancer, and/or where in the CT slice is there a likelihood of lung cancer.

One sub-problem of the technical problem is how to obtain data from the global neural network for combination with outputs of other neural networks. At least some implementations of the systems, methods, apparatus, and/or code instructions described herein provide the solution of computing a heatmap per image from the global neural network that is designed to apply a global operation (e.g., max pooling) to compute an overall classification label for the image (e.g., cancer or no-cancer). Since the global neural network is designed to output a global classification category, extraction of the heatmap from the global neural network posses a technical challenge. For example, the heatmap cannot be obtained from the final classification label output.

Another sub-solution to another sub-problem in addressing the technical problem is how to combine heatmaps outputted by each one of the different neural network components of the model. At least some implementations of the systems, methods, apparatus, and/or code instructions described herein provide the solution of performing a union and/or intersection operation on ROIs of the image extracted based on the heatmaps. The ROIs computed from the union and/or intersection operation are fed into the output component of the model to obtain the final output denoting whether the respective image includes visual findings denoting a medical condition (e.g., cancer) and if so where likelihood of malignancy is located in the image.

At least some implementations of the systems, methods, apparatus, and/or code instructions described herein improve the technology of machine learning models for computing likelihood of visual findings denoting a medical condition such as malignancy in an image, by including a patch-based classifier component in the model. The patch-based classifier may improve the ability and/or accuracy of the model in detecting the visual findings, for example, by using a model with higher depth and/or capacity in comparison to global classifiers and/or local classifiers. The higher depth may be obtained by patch sizes that are substantially smaller than the full image. The high depth patch neural network component is combined with lower depth local and/or global neural network components to provide an overall increase in performance of the model.

Additional differences and/or improvement of the model described herein over existing approaches are now discussed.

In one existing two phased approach, images are processed in serial. In contrast, the model described herein processes the images in parallel by each one of the model components. An exemplary improvement is that if one or more of the components of the model miss detecting an indication of likelihood of malignancy (e.g., visual finding), the other classifier components may detect the likelihood of malignancy (e.g., detect the visual finding). The operation of union and/or intersection of the ROIs compensates for the missed malignancy.

Another existing approach is based on parallel execution of classifiers on the same image. The model described herein correlates prediction results from multiple neural network components and/or classifiers based on the identified locations, which provide the improvement of increasing performance of the model, in contrast to the existing approach. Moreover, different neural network components are used, including the local object detector component (trained on locally annotated data), and a global image classifier component (trained on a global or per-image annotation), and/or a patch classifier component, in contrast to the existing approach.

Yet another existing approach is based on a cascade of classifiers that are run serially. The technical problem with such approach is that the overall sensitivity of the cascade is limited by the sensitivity of its 'weakest chain link', since a false negative ROI is filtered out in one of the stages and is not evaluated again by upstream classifiers. In contrast, the model described herein which includes multiple components that process the image in parallel compensates when any one (or more) of the components incorrectly miss a detection of likelihood of malignancy using the other component(s) that detected the likelihood of malignancy.

In yet another existing approach, a single neural network with two branches is used to analyze medical images. The single neural network with two branches is trained as a whole. In contrast, each component of the model described herein is trained independently, making it more statistically robust.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
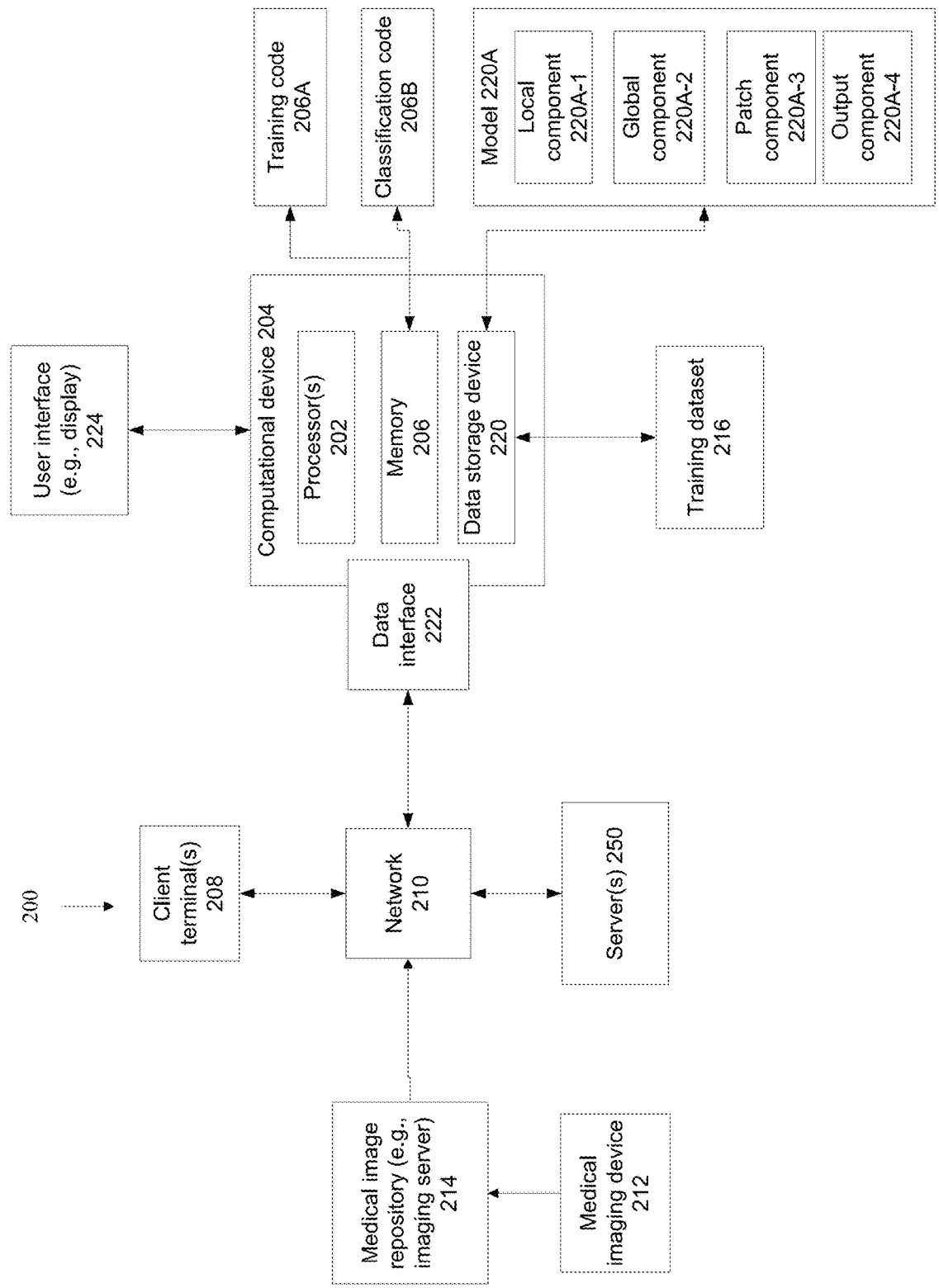
FIG. 2 is a block diagram of components of a system for detection of likelihood of malignancy in an anatomical image of a patient by a model including a global component, a local component, a patch component, and an output component that is fed aggregated ROIs extracted from each of the other components, in accordance with some embodiments of the present invention.
Figure 3:
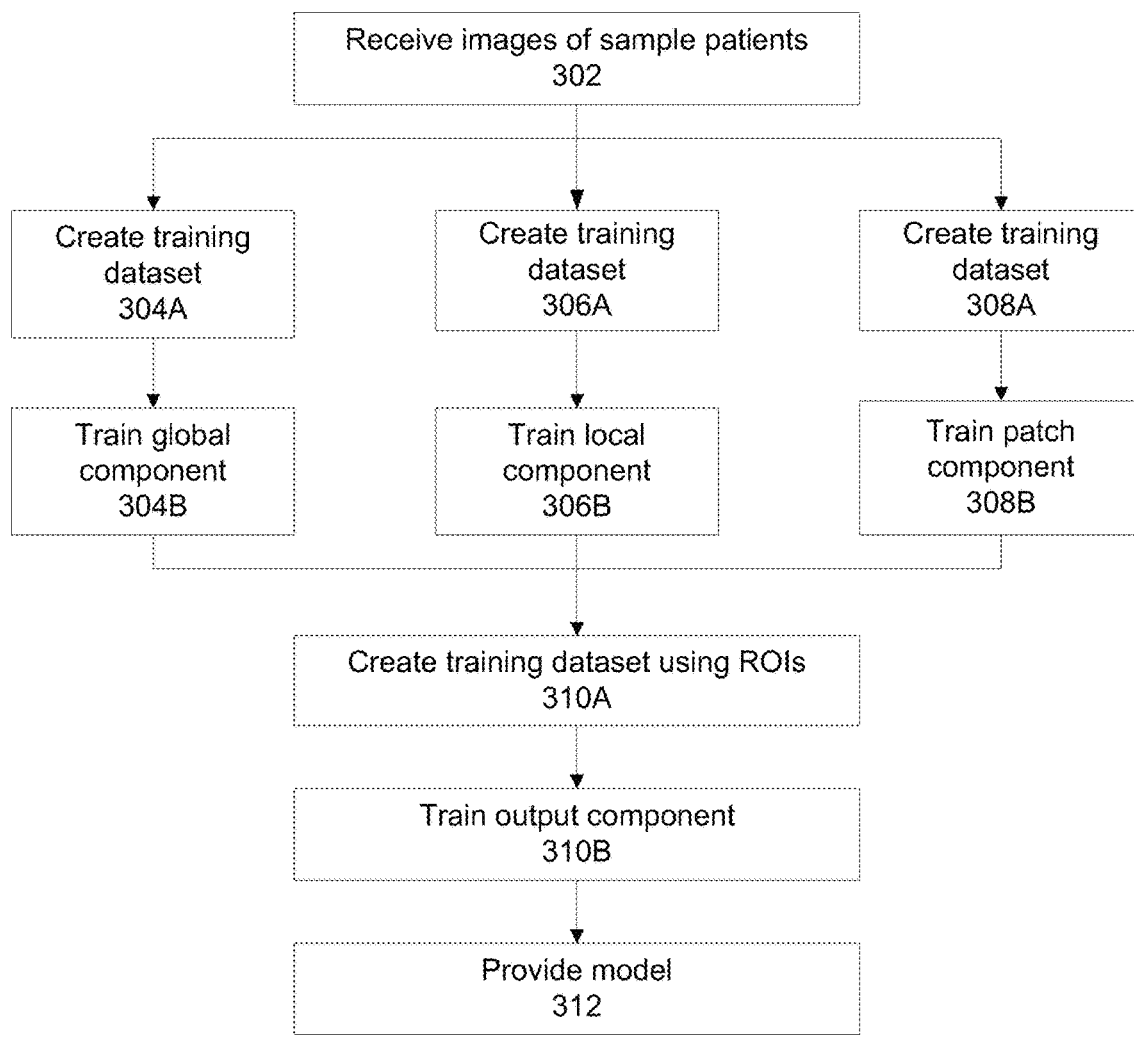
FIG. 3 is a flowchart of a method for training a model including a global component, a local component, a patch component, and an output component that is fed aggregated ROIs extracted from each of the other components, for detection of likelihood of malignancy in an anatomical image, in accordance with some embodiments of the present invention.

Reference is now made to FIG. 1, which is a flowchart of a method for detection of likelihood of malignancy in an anatomical image of a patient by a model including a global component, a local component, a patch component, and an output component that is fed aggregated ROIs extracted from each of the other components, in accordance with some embodiments of the present invention. Reference is also made to FIG. 2, which is a block diagram of components of a system 200 for detection of the likelihood of malignancy in an anatomical image of a patient by a model including a global component, a local component, a patch component, and an output component that is fed aggregated ROIs extracted from each of the other components, in accordance with some embodiments of the present invention. Reference is also made to FIG. 3, which is a flowchart of a method for training a model including a global component, a local component, a patch component, and an output component that is fed aggregated ROIs extracted from each of the other components, for detection of likelihood of malignancy in an anatomical image, in accordance with some embodiments of the present invention. System 200 may implement the features of the method described with reference to FIG. 1 and/or FIG. 3, by one or more hardware processors 202 of a computing device 204 executing code instructions stored in a memory (also referred to as a program store and/or storage device) 206, for example, training code 206A, classification code 206B, and/or model code 220A.

Computing device 204 may be implemented as, for example one or more and/or combination of: a client terminal, a server, a radiology workstation, an imaging server (e.g., PACS), an electronic medical record (EMR) server, a virtual machine, a virtual server, a computing cloud, a mobile device, a desktop computer, a thin client, a Smartphone, a Tablet computer, a laptop computer, a wearable computer, glasses computer, and a watch computer.

Computing device 204 may be implanted as an add-on to clinical software, for example, to a radiology workstation, a PACS server (or other medical imaging storage server), an EMR server, and/or other patient management software.

Computing device 204 may include locally stored software that performs one or more of the acts described with reference to FIG. 1 and/or FIG. 3, and/or may act as one or more servers (e.g., network server, web server, a computing cloud, virtual server) that provides services (e.g., one or more of the acts described with reference to FIG. 1 and/or FIG. 3) to one or more client terminals 208 (e.g., client terminal used by a user for viewing medical images, client terminal running EMR access software, client terminal running patient management software, remotely located radiology workstations, remote picture archiving and communication system (PACS) server, remote electronic medical record (EMR) server) over a network 210, for example, providing software as a service (SaaS) to the client terminal(s) 208, providing an application for local download to the client terminal(s) 208, as an add-on to a web browser and/or a medical imaging viewer application and/or EMR viewing application and/or other patient management application, and/or providing functions using a remote access session to the client terminals 208, such as through a web browser, application programming interface (API), and/or software development kit (SDK).

Computing device 204 receives medical images captured by an imaging device(s) 212, for example, two dimensional images, three dimensional images, a sequence of 2D medical images, and/or a three dimensional (3D) medical imaging device from which 2D images are optionally extracted as slices (e.g., CT, tomosynthesis, MRI). Medical imaging machine(s) 212 may include a mammogram machine, a CT scanner, an MRI machine, a tomosynthesis device, and an ultrasound machine.

Medical images captured by imaging machine 212 may be stored in an imaging repository 214, for example, an imaging storage server, a data storage server, a computing cloud, a PACS server (picture archiving and communication system), and a hard disk. The medical images stored by medical image repository 214 include medical images of patients for analysis, and/or medical images of sample patients included in a training dataset 216 for training the model, as described herein. The images may be globally annotated and/or locally annotated, as described herein.

Computing device 204 may receive the medical image(s) via one or more data interfaces 222, for example, a wire connection (e.g., physical port), a wireless connection (e.g., antenna), a network interface card, other physical interface implementations, and/or virtual interfaces (e.g., software interface, application programming interface (API), software development kit (SDK), virtual network connection).

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 stores code instructions executable by hardware processor(s) 202. Exemplary memories 206 include a random access memory (RAM), read-only memory (ROM), a storage device, non-volatile memory, magnetic media, semiconductor memory devices, hard drive, removable storage, and optical media (e.g., DVD, CD-ROM). For example, memory 206 may store classification code 206B that execute one or more acts of the method described with reference to FIG. 1 and/or training code 206A that execute one or more acts of the method described with reference to FIG. 3.

Classification code 206B may operate a trained model 220A, for example, obtains the image, and/or feeds the image into each component of model 220A.

Model 220A includes a local component 220A-1, a global component 220A-2, an optional patch component 220A-3, and an output component 220A-4, as described herein.

Computing device 204 may include a data storage device 220 for storing data, for example, model 220A as described herein, and/or training dataset 216 as described herein. Data storage device 220 may be implemented as, for example, a memory, a local hard-drive, a removable storage unit, an optical disk, a storage device, a virtual memory and/or as a remote server and/or computing cloud (e.g., accessed over network 210). It is noted that model 220A may be stored in data storage device 220, for example, with executing portions loaded into memory 206 for execution by processor(s) 202.

Computing device 204 may connect using network 210 (or another communication channel, such as through a direct link (e.g., cable, wireless) and/or indirect link (e.g., via an intermediary computing unit such as a server, and/or via a storage device) with one or more of:

Client terminal(s) 208 and/or server(s) 250, for example, when computing device 204 acts as a server providing services (e.g., SaaS) to remote radiology terminals, PACS servers, EMR servers, medical servers and/or other remove devices, by analyzing remotely obtained medical images as described herein.

Server(s) 250, for example, to obtain updates to model 220A.

Medical image repository (e.g., imaging server) 214, for example, to obtain the medical image(s) of the patient for analysis, and/or to obtain medical image(s) of sample patients for inclusion in the training dataset for training the model.

Computing device 204 includes and/or is in communication with a user interface(s) 224 that includes a mechanism designed for a user to enter data (e.g., select patient medical images for analysis) and/or view the analysis. Exemplary user interfaces 224 include, for example, one or more of, a touchscreen, a display, a keyboard, a mouse, and voice activated software using speakers and microphone.

Referring now back to FIG. 1, at 102, a model for outputting a likelihood of malignancy in an anatomical image of a patient is provided and/or trained, for example, as described with reference to FIG. 3.

Different models may be provided, for example, per type of anatomical imaging modality (e.g., CT, x-ray, MRI, nuclear medicine scan, PET, ultrasound), and/or per target tissue and/or per target cancer type (e.g., breast and/or breast cancer, prostate and/or prostate cancer, colon and/or colon cancer, esophagus and/or esophageal cancer, liver and/or liver cancer, pancreas and/or pancreatic cancer, brain and/or brain cancer, lung and/or lung cancer).

At 104, an anatomical image is received. The image may be received, for example, from a PACS server, from a data storage device, from a client terminal, from a removable storage device (e.g., CD ROM, disc on key, USB connected device).

The anatomical image is of a certain patient, depicting one or more target tissues which are being analyzed by the model to detect likelihood of malignancy depicted therein. For example, the anatomical image comprises a mammographic image, and likelihood of malignancy comprises likelihood of breast cancer.

The anatomical image is captured by a certain imaging modality device, as described herein.

The anatomical image may be a 2D image. The 2D image may be directly captured by the imaging modality device, for example, 2D x-rays and/or 2D ultrasound images. The 2D image may be extracted from a 3D imaging dataset, for example, 2D slices, for example, from a CT scan, an MRI scan, and/or a nuclear medicine scan.

At 106, the anatomical image is fed into a global component of a model. The anatomical image may be fed as a whole into the global component.

The global model outputs (i.e., is trained to output) a global classification label indicative of likelihood of malignancy being depicted within the image, optionally anywhere within the image. For example, the global model outputs a probability of malignancy being depicted within the image, for example, within the range of 0% to 100%. In another example, the final output of the global model is a binary value indicative of no malignancy detected within the image, or malignancy detected within the image.

The global component may be implemented as a deep convolutional neural network for image classification, that may end with a global pooling operator (e.g., 2D global max/average pooling operator) and/or a classification head which may be either fully-convolutional or fully-connected. Examples for such architecture implementations include: VGG, ResNet and its variants (ResNet-101, ResNeXt-101, SE-ResNet), Inception and its variants (Xception, Inception-ResNet-v2, Inception-v4).

At 108, the anatomical image is fed into a local component of the model. The anatomical image may be fed as a whole into the local component.

The local component outputs (i.e., trained to output) a localized boundary indicative of a location within the image where malignancy is likely, for example, a bounding box, and/or other geometrical shapes enclosing a region. The boundary may define a region of the image where the entire malignancy is located, or where portions of malignancy above a probability threshold are located (e.g., likelihood of malignancy greater than 70% located within the box). Multiple localized boundaries may be defined for each image. The localized boundaries may overlap and/or be non-overlapping.

The local component may be implemented as a deep convolutional neural network for object detection that outputs bounding boxes along with their corresponding probabilities. Output may be with respect to a fixed set of anchor-boxes, and/or by using a region proposal mechanism. Examples for such architecture implementations include: RetinaNet, Faster R-CNN, YOLOv3, SSD.

At 110, the anatomical image is fed patch-wise into a patch component of the model. The image may be divided into multiple patches, with each patch being fed independently into the patch component (e.g., sequentially, in parallel). Patches may be densely extracted across the image. Patches may overlap with a predefined overlap setting, for example, 30%, 50%, or other values. The overlap may be selected to avoid missing malignant lesions, for example, that are cut and/or lie on an edge between two adjacent patches. Alternatively, patches may be adjacent to one another without overlapping.

Optionally, patches are pre-processed, for selecting patches to feed into the patch component. Non-selected patches are not fed into the patch components. The selection of patches may be performed by a computer-vision heuristic process designed to discards irrelevant patches, for example, patches that include only background and no anatomical regions. Patches below a per-patch-average-intensity threshold may be discarded, for example, all-black patches are discarded. The selection of patches may reduce computational costs of upstream components.

Optionally, the number of patches extracted from the anatomical image is set as a hyperparameter that may be tuned, for example, using training and validation sets to perform hyperparameter tuning.

Optionally, all patches extracted from the anatomical image have the same size. Patch size may be set as a hyperparameter that may be tuned, for example, using training and validation sets. The size of the patch may be selected to correspond to the average lesion size of the context domain. For example, in mammograms, patch size may be selected with respect to an average lesion size. Patch size may be selected such that most lesions are fully contained inside a respective patch. Larger lesions are detected using their partial crops (since malignant visual features are typically "local" and do not require having the entire lesion in the field of view).

Patches may be independently processed by the patch component.

The patch component outputs (i.e., is trained to output) a patch level classification label for each patch, for example, a probability of malignancy being depicted within the respective patch, and/or a binary value indicative of no malignancy detected within the respective patch, or malignancy detected within the respective patch.

The patch component may be implemented as neural network. Optionally, the patch component neural network is deeper than the neural network implementations of the global and/or local components. Optionally, a number of neural network layers of the patch component is higher than a number of neural network layers of the global component and is higher than a number of neural network layers of the local component. Optionally, the number of patches per mini-batch is higher than an implementation of the global and/or network components that is based on patch analysis of images.

It is noted that 106, 108, and 110 may be implemented independently of one another, optionally in any order, for example, 106, 108, and 110 may be executed sequentially in any order and/or 106, 108, and 110 may be executed in parallel.

At 112, a respective set of ROIs is extracted from each one of the global, local, and patch components. Each ROI is indicative of a region of the anatomical image likely to include an indication of malignancy, for example, the regions in the image representing highest probability of malignancy.

Optionally, a same number of ROIs is extracted for each one of the global component, the local component, and the patch component. The number of extracted ROIs may be defined, for example, manually entered by a user, set as a system default value, and/or automatically computed (e.g., optimal value based on current results and/or previous results).

The same number of ROIs may be extracted, for example, even when some of the components contradict each other, for example, one or more components identify likelihood of malignancy in the image, and other components do not identify likelihood of malignancy in the image. In this manner, the components reduce risk of missing malignancy in the image, even when a certain component misses the malignancy.

Optionally, ROIs extracted for each one of the components are disjoint, without an intersection between ROIs extracted for each one of components. Alternatively, at least some ROIs intersect each other.

Extracting ROIs from the global component represents a technical challenge. The global component includes a global pooling operation layer (or other similar layer) after which the ROIs cannot be detected, for example, the final output is a single value for the image as a whole which cannot be used to obtain data for the ROI. Different processes may be used to extract data from internal (e.g., hidden) layers of the global component for generating the ROIs denoting locations likely depicting malignancy. One or more of the processes may be based on extracting data from hidden layers of the global component to compute a heat map, where intensity values of the heat map (e.g., pixels) correspond to likelihood of malignancy. For example the ROIs of the global component may be computed by a fully-convolutional classifier after the global pooling operation layer. A fully-convolutional classifier head may be re-applied at each location of the last feature map. In another example, the ROIs of the global component may be computed by a back propagation method, for example, Grad-CAM or derivates thereof. In yet another example, the ROIs of the global component may be computed by occluding different areas of the anatomical image and re-running the anatomical image with occluded area(s) through the global component to determine which occluded areas correlate with the largest difference in score indicative of malignancy. The occluded area(s) are designated as the ROIs.

Optionally, one or more of the following data are outputted by each of the global, local, and patch components. The data may be stored as metadata.

Image identifier

ROI location within the image, for example, denoted as pixel coordinates relative to the image, for example, (x1, y1, x2, y2) for a rectangular boundary box, where (x1, y1) denote the left lower corner of the ROI and (x2, y2) denote the upper right corner of the ROI.

Score indicative of likelihood of malignancy depicted within the respective ROI, for example, a value in the range [0, 1] such as a probability value.

At 114, the ROIs from each one of the global, local, and patch components are aggregated into an aggregated set of ROIs. The aggregation of the ROIs may be performed by an intersection operation and/or a union operation, which is performed on the ROIs from each one of the components.

The number of ROIs in the aggregated set is between the same number of ROIs outputted by each component (i.e., when the ROIs outputted by each component intersect perfectly with one another then aggregating the three sets of ROIs results in a single set of ROIs) and three times the same number of ROIs outputted by each component (i.e., when the ROIs outputted by each component are disjoint and do not overlap at all with each other, aggregating the ROIs results in the same disjoint ROIs).

Optionally, a threshold is defined for intersecting the ROIs to create the aggregated set of ROIs. For example, two ROIs intersect (i.e., are aggregated) with each other if and only if (iff) the equation intersection/union>=T, where T denotes a predefined threshold.

The follow is an example of pseudocode for merging of the ROIs from the global, local, and patch components to create the aggregated set of ROI (K denotes the same number of ROIs extracted from each component, and the metadata is as described with reference to 112):

ROI_id=0 # an id of a "merged ROI"
    For i in {0,1,2}: # for each of the three components (global, local, patch)
        For j in range(K): # for each of the K ROIs
            Create the metadata for a merged ROI with id==ROI_id
            Denote ROI j of component i as the current ROI (P0)
            For the certain ROI, find ROIs with the largest intersection from the two other components' ROI lists—denote these two other ROIs as P1 and P2, respectively (there may be cases in which the current ROI does not intersect with any of the other ROIs—in this case, P1 and P2 are Null)
        ROI_id+=1

At 116, the aggregated set of ROIs is fed into an output component of the model.

The output component may be implemented as a classifier model designed for tabular data, for example, as an XGBoost classifier, and/or a random forest classifier.

Optionally, each ROIs of each component is associated with a score indicative of likelihood of malignancy depicted therein.

Each aggregated ROI may include a vector of scores for the respective global, local, and patch components. The vector is fed into the output component.

The following is an example of metadata denoting the aggregated set of ROIs that is fed into the output component:
    ROI id
    Image id
    (x1, y1, x2, y2)—(x1, y1) denotes the lower left corner of the aggregated ROI (i.e., union over the three ROIs from the three components) and (x2, y2) denotes the upper right corner of the aggregated ROI.
    Malignancy score tuple (score_0, score_1, score_2)—if P1 or P2 is Null, then the relevant malignancy score is zero
    Intersection/union (P0, P1)—or Null if P0 and P1 are disjoint
    Intersection/union (P0, P2)—or Null if P0 and P2 are disjoint
    Intersection/union (P1, P2)—or Null if P1 and P2 are disjoint
    Intersection/union (P0, P1, P2)—or Null if P0, P1 and P2 are disjoint At 118, the output component outputs an indication of likelihood of malignancy, for example, a probability value indicative of malignancy, and/or a binary value (e.g., no malignancy or malignancy present).

Optionally, the output component outputs a score indicative of likelihood of malignancy for the anatomical image as a whole. Alternatively or additionally, the output component computes an aggregation score for each aggregation ROI indicative of likelihood of malignancy for the respective aggregation ROI.

At 120, the indication of likelihood of malignancy is provided, for example, presented on a display, stored as metadata associated with the medical image (e.g., in the PACS server), stored in a field in the electronic health record of the patient, used to mark the image (e.g., ROIs associated with likelihood of malignancy such as above a threshold are color coded and/or marked such as with an arrow), and/or forwarded to another storage device and/or server.

At 122, the patient may be diagnosed according to the indication and/or treatment of the patient is planned according to the indication. The patient may be treated according to the indication. For example, additional imaging of the patient may be performed, a biopsy may be performed, surgery may be performed, chemotherapy may be administered, radiation therapy may be administered, and/or a watch and wait approach may be selected.

Referring now back to FIG. 3, at 302, anatomical images for multiple sample patients is received, for example, from the PACS server, from the anatomical imaging device, and/or from another storage device.

The anatomical images include normal and/or non-malignancy images, images known to depict malignancy.

At 304A, a set of training images is created, where each image is labeled with an image level classification label. The label is for the image as a whole. The label may include, for example, an indication of malignancy present in the image, or no malignancy in the image.

The labeling may be performed manually (e.g., by a user manually reviewing the images and/or the radiologist reports) and/or automatically (e.g., by code that automatically analyzes radiology reports and/or extracts a value from the electronic health record).

At 304B, the global component of the model is trained using the set of training images and labels of 304A.

At 306A, a set of training images is created, where each image is annotated with a localized boundary denoting a location associated with likelihood of malignancy, for example, a boundary box (or other geometrical figure) is drawn on the image depicting malignancy therein. The boundary box may be manually marked and/or drawn by a user, for example, using a touch screen and/or graphic user interface (GUI).

At 306B, the local component of the model is trained using the set of training images and boundary boxes of 306A.

At 308A, a set of training images is created, where each image is divided into multiple patches. Patches may overlap (e.g., by a defined value, such as 30%, or 50%, or other value) or may not overlap (e.g., adjacent). Each patch is associated with a corresponding patch level classification label, for example, an indication of malignancy present in the respective patch, or no malignancy in the respective patch. The patch labels may be assigned by setting a threshold for intersection between the patch and the malignant lesion, for example, if at least 30%, or 40%, or 50%, or other smaller, intermediate, or larger percentage, of lesion area is contained within a respective patch, then the respective patch is marked as malignant; otherwise it is marked as non-malignant/normal.

At 308B, a patch component of the model is trained using the set of training patches and labels of 308A.

It is noted that for 304A, 306A, and 308A, the same images may be used, where the labeling and/or division into patches is as described for each component. Alternatively or additionally, different images sets may be used (e.g., for different patients).

Each one of the global component, local component, and patch component may be trained independently (i.e., as in 304B, 306B, and 308B), for example, no data flows between the different components, and/or each component is trained using its own respective loss function.

At 310A, a set of training aggregated regions of interest (ROIs) is created by aggregating ROIs extracted from each one of the global, local, and patch components (e.g., as described with reference to 112 and 114 of FIG. 1). Each ROI is indicative of a region of the anatomical image having likelihood of malignancy.

Labels for the aggregated ROIs may be obtained from previously labeled images and/or patches, and/or created manually and/or automatically.

At 310B, the output component of the model is trained using the aggregated ROIs and associated ground truth labels of 310A.

At 312, the global, local, patch, and output components of the model are provided, for example, stored in a data storage device and/or transmitted to another computing device.

In response to feeding a target anatomical image into the model (i.e., into the global, local, and patch components), the output component outputs an indication of the likelihood of malignancy, as described herein.

Figure 4:
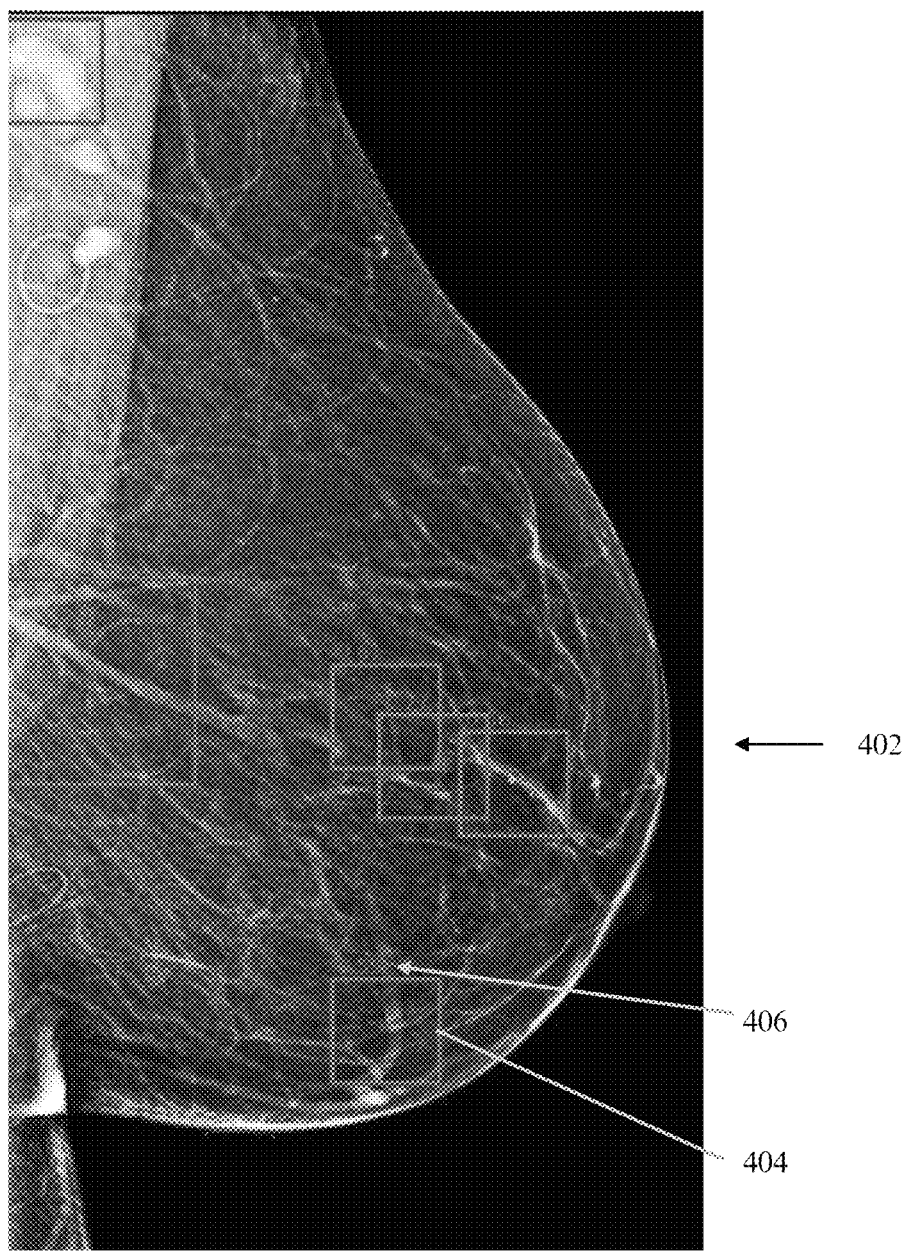
FIG. 4 is a schematic of an exemplary output of the local component of the model for an input of a mammogram, in accordance with some embodiments of the present invention.

Reference is now made to FIG. 4, which is a schematic of an exemplary output of the local component of the model for an input of a mammogram, in accordance with some embodiments of the present invention. Local component outputs one or more boundary boxes (one box 404 marked as an example) denoting likelihood of malignancy therein, optionally with an associated value (a value (i.e., 0.59) 406 is marked for box 404), for example, probability of malignancy therein. Boundary boxes may be marked on image 402 (a mammographic image is depicted as an example).

Figure 5:
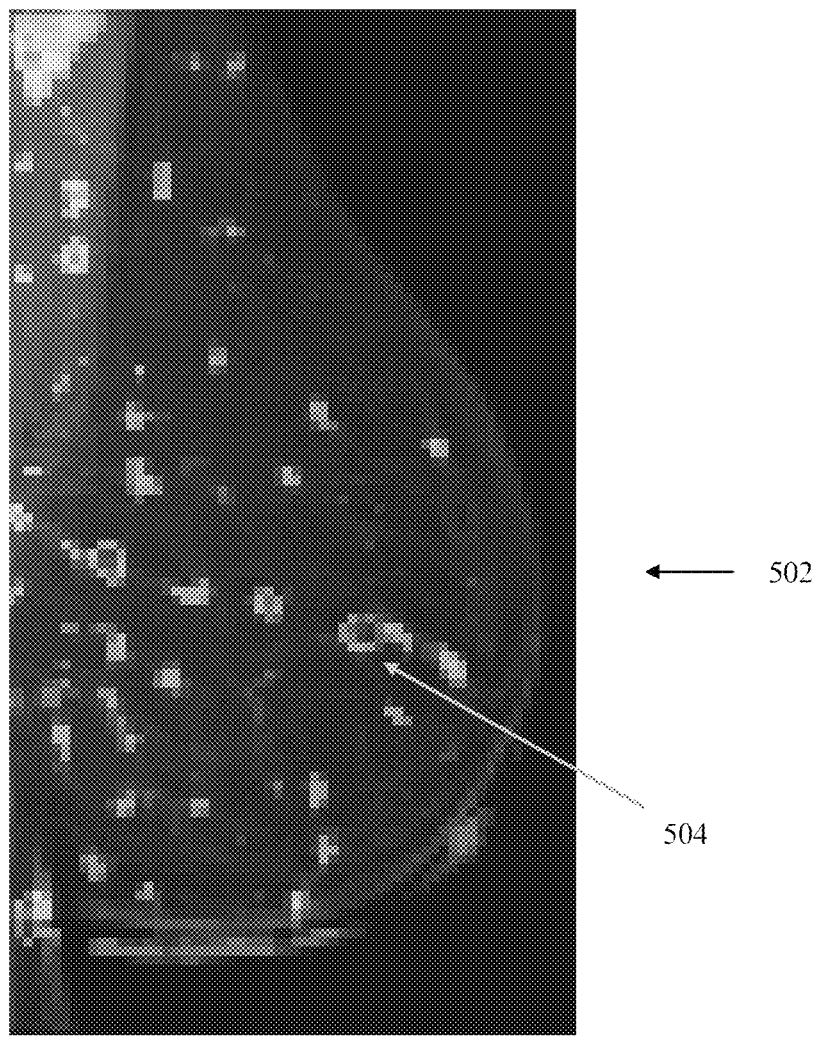
FIG. 5 is a schematic of an exemplary heatmap extracted from internal layers of the global component of the model, used to compute ROIs, for the input of the mammogram, in accordance with some embodiment of the present invention.

Reference is now made to FIG. 5, which is a schematic of an exemplary heatmap 502 extracted from internal layers of the global component of the model, used to compute ROIs, for the input of the mammogram, in accordance with some embodiment of the present invention. "Hot" pixels denote locations in the image having relatively increased likelihood of representing malignancy (e.g., one "hot" region 504 is marked as an example).

Figure 6:
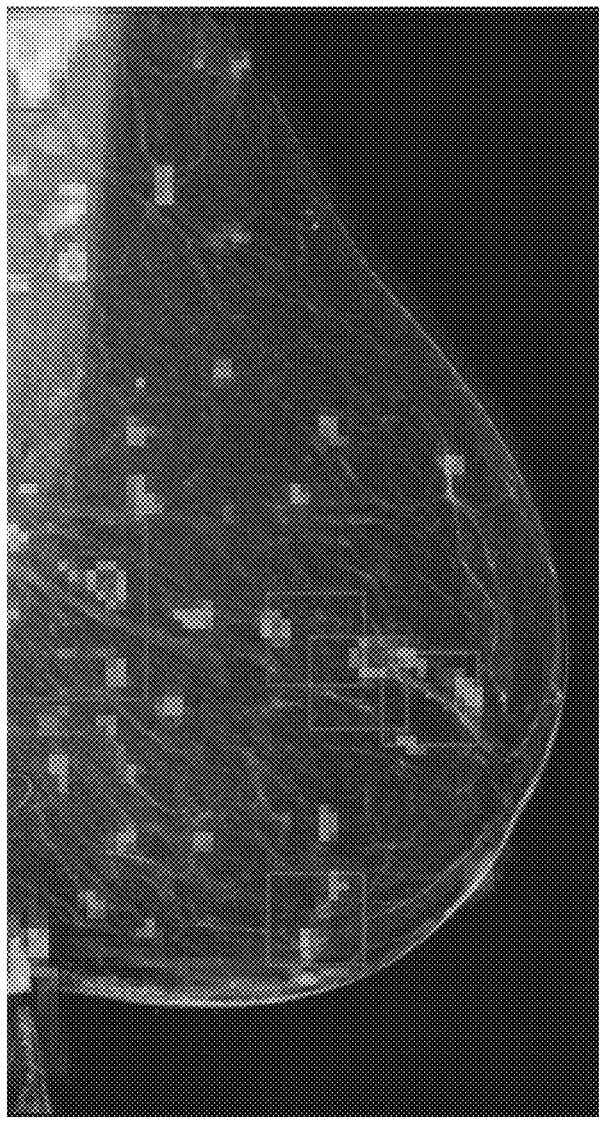
FIG. 6 is a schematic created from the image FIG. 4 (outputted by the local component) overlaid over the heatmap of FIG. 5 (outputted by the global component), for depicting that the "hot" spots in the heatmap corresponding to the boundary boxes of mammogram image, in accordance with some embodiment of the present invention.

Reference is now made to FIG. 6, is a schematic created from image 402 of FIG. 4 (outputted by the local component) overlaid over heatmap 502 of FIG. 5 (outputted by the global component), for depicting that the "hot" spots in heatmap 502 corresponding to boundary boxes of mammogram image 402, in accordance with some embodiment of the present invention. The overlapping hot spots and boundary boxes are more likely to represent malignancies. Hot spots and boundary boxes that do not overlap may represent a miss of the malignancy by one of the components, or may represent errors in classification by one of the components.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant anatomical images and neural networks will be developed and the scope of the terms anatomical images and neural networks are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method for detection of likelihood of malignancy in an anatomical image of a patient for planning treatment thereof, comprising:
    receiving an anatomical image;
    feeding the anatomical image into a global component of a model trained to output a global classification label;
    feeding the anatomical image into a local component of the model trained to output a localized boundary;
    feeding the anatomical image patch-wise into a patch component of the model trained to output a patch level classification label;
    extracting three sets of regions of interest (ROIs), each is a respective set of ROIs extracted from a respective one of the global, local and patch components, each ROI indicative of a region of the anatomical image likely to include an indication of malignancy;
    accumulating the ROIs from the three sets of ROIs and aggregating the accumulated ROIs into an aggregated set of ROIs; and
    feeding the aggregated set of ROIs into an output component that outputs an indication of likelihood of malignancy, wherein treatment of the patient is planned according to the indication.

2. The computer implemented method of claim 1, wherein the anatomical image comprises a mammographic image, and likelihood of malignancy comprises likelihood of breast cancer.

3. The computer implemented method of claim 1, wherein a same number of ROIs extracted for each one of the global component, the local component, and the patch component.

4. The computer implemented method of claim 3, wherein a number of ROIs in the aggregated set is between the same number and three times the same number.

5. The computer implemented method of claim 1, wherein the aggregation of the ROIs is performed by at least one of an intersection operation and a union operation, performed on the ROIs from each one of the components.

6. The computer implemented method of claim 1, wherein the output component outputs a score indicative of likelihood of malignancy for the anatomical image as a whole.

7. The computer implemented method of claim 1, wherein ROIs extracted for each one of the components are disjoint, without an intersection between ROIs extracted for each one of the components.

8. The computer implemented method of claim 1, wherein each ROIs is associated with a score indicative of likelihood of malignancy depicted therein, wherein each aggregated ROI includes a vector of scores of the respective components, and wherein the vector is fed into the output component, wherein the output component computes an aggregation score for each aggregation ROI indicative of likelihood of malignancy for the respective aggregation ROI.

9. The computer implemented method of claim 1, wherein the global component includes a global pooling operation layer after which the ROIs cannot be detected.

10. The computer implemented method of claim 9, wherein the ROIs of the global component are computed by a fully-convolutional classifier after the global pooling operation layer, and re-applying the fully-convolutional classifier at each location of the last feature map.

11. The computer implemented method of claim 9, wherein the ROIs of the global component are computed by a back propagation method.

12. The computer implemented method of claim 9, wherein the ROIs of the global component are computed by occluding different areas of the anatomical image and re-running the anatomical image with occluded area through the global component to determine which occluded areas correlate with the largest difference in score indicative of malignancy.

13. The computer implemented method of claim 1, wherein a number of neural network layers of the patch component is higher than a number of neural network layers of the global component and is higher than a number of neural network layers of the local component.

14. The computer implemented method of claim 1, wherein each one of the global component, the local component, the patch component, and the output component are implemented as neural networks.

15. A computer implemented method for training a model for detection of an indication of malignancy in an anatomical image of a target individual, comprising:
    training a global component of the model using a set of training images each labeled with an image level classification label;
    training a local component of the model using a set of training images each annotated with a localized boundary denoting a location associated with likelihood of malignancy;
    training a patch component of the model using a set of training images each divided into a plurality of patches associated with corresponding patch level classification labels;
    training an output component of the model using a set of training aggregated regions of interest (ROIs) created by accumulating three sets of ROIs, each of the three sets of ROIs is extracted from a respective one of the global, local and patch components, each ROI indicative of a region of the anatomical image having likelihood of malignancy, and associated ground truth labels; and
    providing the global, local, patch, and output components of the model, wherein in response to feeding a target anatomical image into the model, the output component outputs an indication of the likelihood of malignancy.

16. The computer implemented method of claim 15, wherein each one of the global component, local component, and patch component are trained independently.

17. A system for detection of likelihood of malignancy in an anatomical image of a patient for planning treatment thereof, comprising:
    at least one hardware processor executing a code for:
        receiving an anatomical image;
        feeding the anatomical image into a global component of a model trained to output a global classification label;
        feeding the anatomical image into a local component of the model trained to output a localized boundary;
        feeding the anatomical image patch-wise into a patch component of the model trained to output a patch level classification label;
        extracting three sets of regions of interest (ROIs), each is a respective set of ROIs extracted from a respective one of the global, local and patch components, each ROI indicative of a region of the anatomical image likely to include an indication of malignancy;

accumulating the ROIs from the three sets of ROIs and aggregating the accumulated ROIs into an aggregated set of ROIs; and feeding the aggregated set of ROIs into an output component that outputs an indication of likelihood of malignancy, wherein treatment of the patient is planned according to the indication.

18. The system of claim 17, wherein the at least one hardware processor further executes a code for:

training the global component of the model using a set of training images each labeled with an image level classification label;

training the local component of the model using a set of training images each annotated with a localized boundary denoting a location associated with likelihood of malignancy;

training the patch component of the model using a set of training images each dividing into a plurality of patches associated with corresponding patch level classification labels; and training the output component of the model using a set of training aggregated regions of interest (ROIs) created by aggregating ROIs extracted from each one of the components and an image level classification label.

19. The computer implemented method of claim 1, wherein the global component of the model, the local component of the model and the patch component of the model process the fed anatomical image in parallel.

20. The computer implemented method of claim 1, wherein feeding the anatomical image patch-wise into the patch component comprising:

dividing the anatomical image into a plurality of patches;

pre-processing the plurality of patches, using computer-vision heuristic process, to select a sub-set of the plurality of patches by discarding irrelevant patches; and feeding the selected sub-set of the plurality of patches into the patch component of the model.

* * * * *